United States Patent
Kishida

(10) Patent No.: US 9,033,501 B2
(45) Date of Patent: May 19, 2015

(54) OPHTHALMOLOGIC IMAGING APPARATUS AND OPHTHALMOLOGIC IMAGING METHOD

(71) Applicant: CANON KABUSHIKI KAISHA, Tokyo (JP)

(72) Inventor: Nobuyoshi Kishida, Musashino (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/873,062

(22) Filed: Apr. 29, 2013

(65) Prior Publication Data

US 2013/0242260 A1  Sep. 19, 2013

Related U.S. Application Data

(63) Continuation of application No. 12/857,876, filed on Aug. 17, 2010, now Pat. No. 8,449,112.

(30) Foreign Application Priority Data

Aug. 27, 2009  (JP) ................................. 2009-196997

(51) Int. Cl.
  *A61B 3/14*  (2006.01)
  *G03B 9/08*  (2006.01)
  *H04N 3/14*  (2006.01)
  *A61B 3/12*  (2006.01)

(52) U.S. Cl.
  CPC .. *A61B 3/12* (2013.01); *A61B 3/145* (2013.01)

(58) Field of Classification Search
  USPC ................. 351/208, 205, 200, 206, 210, 246;
         396/452, 456, 480, 246–247, 235, 357;
         348/294, 296, 297, 302–305, 333.01,
         348/362, 363, 366, 200.1, 221.1
  See application file for complete search history.

(56) References Cited

U.S. PATENT DOCUMENTS 7,290,882 B2 * 11/2007 Collins et al. ................. 351/218
2007/0183760 A1 * 8/2007 Mizuno et al. ................. 396/18

* cited by examiner

*Primary Examiner* — Dawayne A Pinkney
(74) *Attorney, Agent, or Firm* — Canon U.S.A., Inc. IP Division

(57) ABSTRACT

An ophthalmologic imaging apparatus includes an observation light source configured to generate infrared light for illuminating a subject's eye via an illumination optical system, an imaging unit configured to receive light returned from the subject's eye via an imaging optical system, and an electronic shutter control unit configured to refresh charge generated caused by light received by the imaging unit in response to turning off of the observation light source.

35 Claims, 8 Drawing Sheets

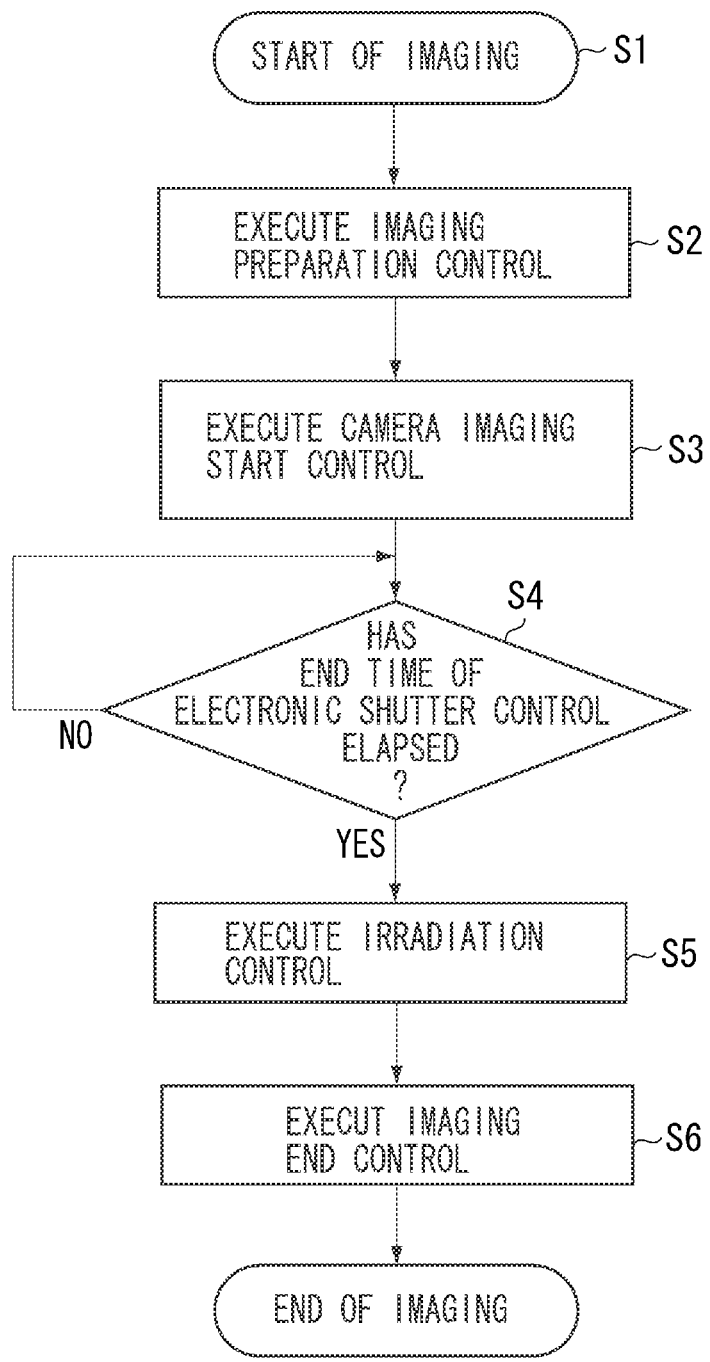

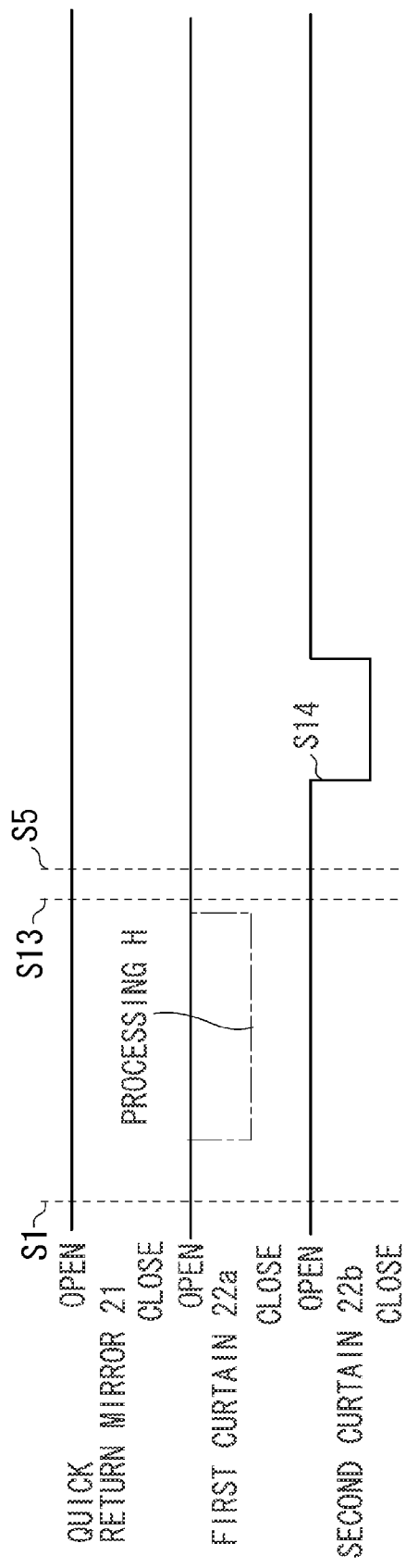

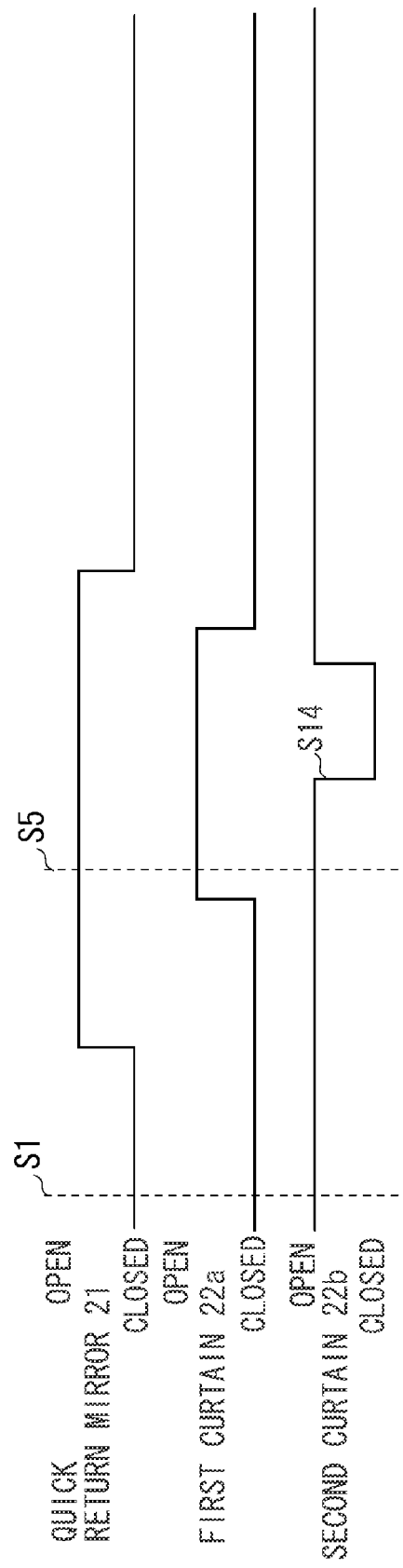

OPHTHALMOLOGIC IMAGING APPARATUS AND OPHTHALMOLOGIC IMAGING METHOD

CROSS REFERENCE TO RELATED APPLICATIONS

This application is a Continuation of U.S. patent application Ser. No. 12/857,876 filed Aug. 17, 2010, which claims priority to Japanese Patent Application No. 2009-196997 filed Aug. 27, 2009, both of which are hereby incorporated by reference in their entireties.

BACKGROUND OF THE INVENTION

1. Field of the Invention

The present invention relates to an ophthalmologic imaging apparatus for imaging a subject's eye.

2. Description of the Related Art

As an ophthalmologic imaging apparatus, a fundus camera that performs fundus imaging of a subject's eye is widely known. As the fundus camera, a non-mydriatic fundus camera is frequently used, which illuminates the fundus with visible light to perform fundus imaging at the moment when a still image is captured while using near infrared light by which a subject's eye does not feel glare during observation.

In this non-mydriatic fundus camera, a sensor that allows observation and imaging is incorporated in the fundus camera. Thus, miniaturization of the apparatus is realized. Further, Japanese Patent Application Laid-Open No. 9-308610 discusses a fundus camera in which a frequent and inconvenient adjustment of the amount of light for observation of a subject's eye having different reflectivities is improved while shortening a period of time from the operation of an imaging switch to acquisition of an image.

Further, a mydriatic fundus camera is also frequently used in which a mydriatic agent is instilled into a subject's eye to perform a precise fundus examination and fundus imaging using visible light both during observation and imaging.

A mydriatic/non-mydriatic-integrated type fundus camera is known, which integrates the mydriatic fundus camera with the above described non-mydriatic fundus camera to realize a multi-functionality. Furthermore, a fundus camera is discussed in Japanese Patent Application Laid-Open No. 9-66030, which is changed into visible observation at the time of mydriatic and infrared observation at the time of non-mydriatic by a mydriatic/non-mydriatic function change unit.

Recently, digitization has become easy. Thus, a digital camera, which is generally used, is frequently used as an imaging camera of a fundus camera. Particularly, a single-lens reflex digital camera is used is because it allow remote imaging from the fundus camera, and it is excellent in compatibility with a film-type camera up to now, and also is sufficient in resolution as an ophthalmologic diagnosis image. Further, since it is commonly used, many single-lens reflex digital cameras have high resolution and latest functional sensor.

A recent fundus camera includes the live view function that is used at the time of observation during which alignment and focus adjustment are performed. However, in Japanese Patent Application Laid-Open No. 9-308610, a sensor capable of observation and imaging is incorporated in the fundus camera. Thus, a digital camera, which is generally used, is not used.

Further, in the fundus camera discussed in Japanese Patent Application Laid-Open No. 9-66030, a charge coupled device (CCD) for performing observation at the time of non-mydriatic imaging and the observation optical system thereof are included. Thus, an image sensor for observation and an image sensor for imaging are needed.

SUMMARY OF THE INVENTION

The present invention is directed to an ophthalmologic imaging apparatus including a mydriatic, non-mydriatic, or mydriatic/non-mydriatic-integrated type ophthalmologic imaging apparatus provided having a live view function.

According to an aspect of the present invention, an ophthalmologic imaging apparatus includes an observation light source configured to generate infrared light for illuminating a subject's eye via an illumination optical system, an imaging unit configured to receive light returned from the subject's eye via an imaging optical system, and an electronic shutter control unit configured to refresh charge generated caused by light received by the imaging unit in response to turning off of the observation light source.

According to another aspect of the present invention, a camera attachable to and detachable from an ophthalmologic imaging apparatus containing an illumination optical system configured to emit infrared light generated from an observation light source to a subject's eye, and an imaging optical system configured to guide light returned from the subject's eye, the camera includes an imaging unit configured to receive light returned from the subject's eye via the imaging optical system, and an electronic shutter control unit configured to refresh charge generated caused by light received by the imaging unit in response to turning off of the observation light source.

An ophthalmologic imaging apparatus according to the present invention executes observation using a live view function of a digital camera, which is generally used, and imaging control using electronic shutter control during imaging. Thus, the time period from when an examiner performs an imaging start operation until imaging is actually performed is minimized. Accordingly, a movement of a fixation position of a subject's eye and an occurrence of the blinks at the moment of imaging can be prevented. Thus, failure of imaging is reduced.

Further, a digital camera, which is generally used, is used, thereby following the advance of a high resolution sensor, and using the live view function for observation. Thus, there is no need to configure a dedicated sensor such as a CCD for executing observation and an observation optical system. Thus, an apparatus can be miniaturized.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 3A and 3B illustrate flowcharts illustrating a flow of operations during imaging according to the first exemplary embodiment of the present invention.

FIGS. 4A, 4B illustrate timing charts of an imaging camera according to the first exemplary embodiment of the present invention.

DESCRIPTION OF THE EMBODIMENTS

Recently, a live view function has been added, which uses the single-lens reflex digital camera not only for still image recording, but also for moving image observation and moving image recording. Generally, the live view function allows imaging without looking into a finder. Thus, there is an advantage in increasing the degree of freedom of an imaging angle.

However, the non-mydriatic fundus camera is configured so as to illuminate the fundus by visible light to execute fundus imaging at the moment when a still image is captured while using near infrared light by which a subject's eye does not feel glare during observation. Thus, a timing signal of visible light illumination during imaging is required. As the timing signal, an open signal is used which is an X contact signal of a shutter screen of the digital camera, which is generally used. When the live view function is used, the shutter screen is in an open state. Thus, when the above-described timing signal is required, the shutter screen needs to be once returned from the open state to a closed state at the moment of imaging.

Accordingly, when observation and imaging of the subject's eye are performed using the live view function on the digital camera that is generally used, time will be required from when an examiner performs an imaging start operation until when imaging is actually performed. Consequently, at the moment of imaging, a fixation position of the subject's eye may move and the blinks may occur. Thus, this may cause failure of imaging.

An ophthalmologic imaging apparatus according to the present invention executes observation using a live view function of a digital camera, which is generally used, and imaging control using electronic shutter control during imaging. Thus, the time period from when an examiner performs an imaging start operation until imaging is actually performed is minimized. Accordingly, a movement of a fixation position of a subject's eye and an occurrence of the blinks at the moment of imaging can be prevented. Thus, failure of imaging is reduced. Further, a digital camera, which is generally used, is used, thereby following the advance of a high resolution sensor, and using the live view function for observation. Thus, there is no need to configure a dedicated sensor such as a CCD for executing observation and an observation optical system. Thus, an apparatus can be miniaturized.

Various exemplary embodiments, features, and aspects of the invention will be described in detail below with reference to the drawings.

Figure 1:
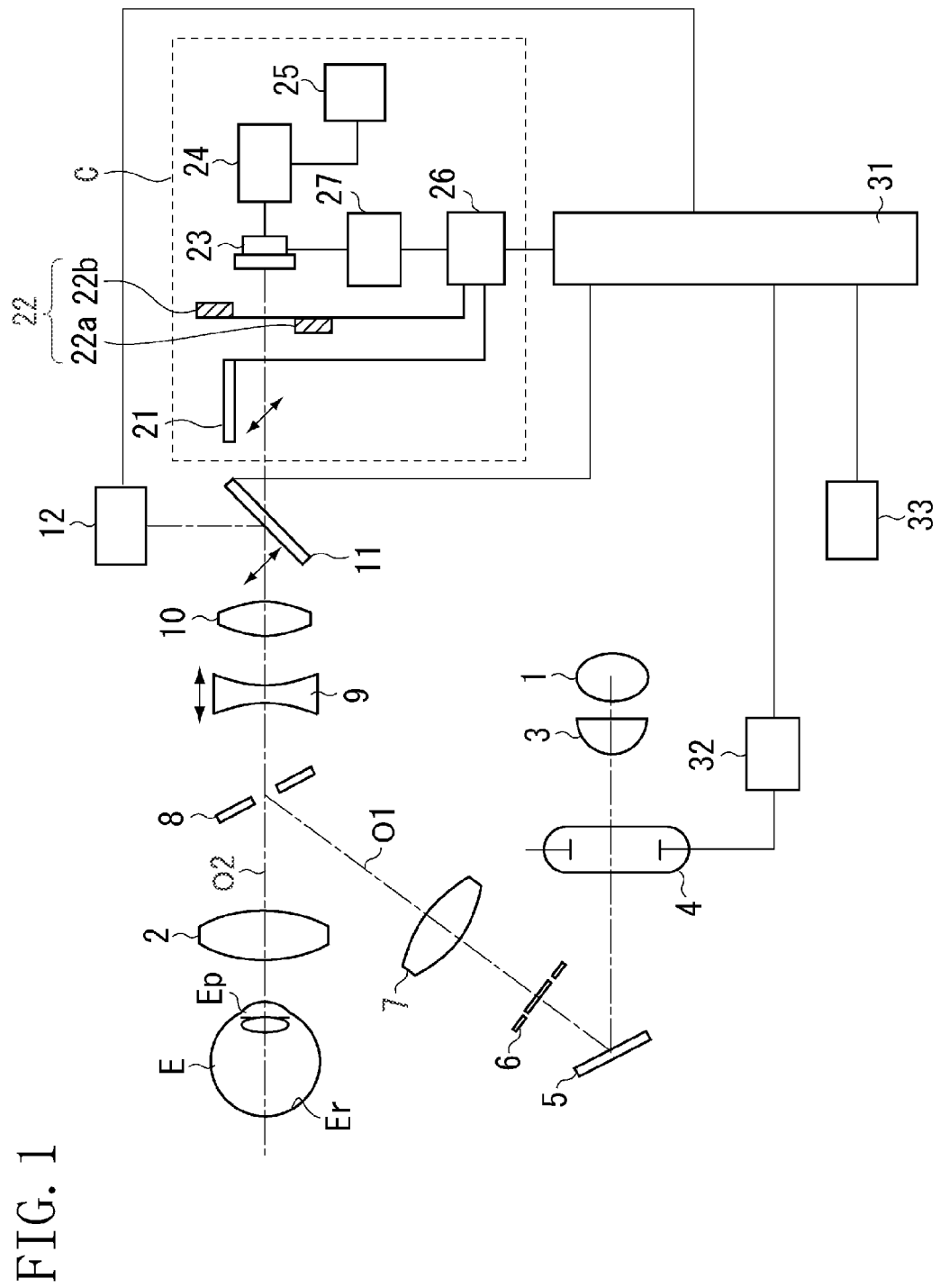
FIG. 1 is a configuration diagram illustrating a non-mydriatic fundus camera according to a first exemplary embodiment of the present invention.

FIG. 1 is a configuration diagram illustrating a fundus camera as an ophthalmologic imaging apparatus according to a first exemplary embodiment of the present invention.

The fundus camera is a non-mydriatic type fundus camera. An imaging camera C is attached behind the fundus camera. On an optical path from an observation light source 1, which is a fundus illumination optical system O1 of the fundus camera, to an objective lens 2 opposing an eye E to be examined, a condenser lens 3, an imaging light source 4, a mirror 5, a diaphragm 6 having a ring opening, a relay lens 7, and a perforated mirror 8 are arranged in order.

On an optical path of a fundus imaging optical system O2 in a direction transmitting through the perforated mirror 8, a focus lens 9, an imaging lens 10, a quick return mirror 11, and the imaging camera C are arranged. The observation light source 1 is a light emitting diode (LED) light source that emits infrared light. The quick return mirror 11 has the characteristic of transmitting infrared light and reflecting visible light. Further, in a direction of reflection from the quick return mirror 11, an internal fixation lamp 12, in which radiation elements such as LEDs for guiding fixation of the eye E to be examined, are arranged.

On the other hand, on the front of the perforated mirror 8, though not illustrated, the LED light source to be used as an alignment index and the emission end of a light guide, which guides the luminous flux to the eye E to be examined, and an alignment index projection system configured to project the alignment index onto the fundus of the subject's eye are provided. Similarly, though not illustrated, in the optical path on the fundus illumination optical system O1, a focus index projection system configured to project a focus index on the fundus Er of the eye E to be examined is provided.

As described in the related art, the imaging camera C in the present exemplary embodiment is a single-lens reflex digital camera. The imaging camera C is attached to the above-described fundus camera and further configured so as to be detachable. On the extension of the optical path in the imaging camera C of the fundus imaging optical system O2, a quick return mirror 21, a first curtain 22a and a second curtain 22b of a shutter screen 22 for controlling the state of exposure, and an image sensor 23 are arranged.

Further, in the imaging camera C, output of the image sensor 23 is connected to a moving image observation monitor 25 including the LCD or the like via a moving image generation unit 24. Furthermore, the output of the image sensor 23 is connected to an imaging camera control unit 26 configured to execute control of the imaging camera C. Still furthermore, outputs of the imaging camera control unit 26 are connected to the image sensor 23, the mirror 21, and the shutter screen 22 via an electronic shutter control unit 27 configured to execute electronic shutter control.

Further, in the fundus camera, a system control unit 31 configured to execute control of the whole fundus camera is included. The system control unit 31 is connected with the imaging camera control unit 26 on the imaging camera C. Outputs of the system control unit 31 are connected to the quick return mirror 11 and further connected to the imaging light source 4 via an imaging light source control unit 32. Furthermore, the system control unit 31 includes an imaging start switch and is connected with an output of an input unit 33 configured to execute still image capturing of the eye E to be examined.

At the time of alignment, infrared light emitted from the observation light source 1 passes through the condenser lens 3 and the imaging light source 4, and is reflected by the mirror 5. The reflected light by the mirror 5 passes through the diaphragm 6 and the relay lens 7, and reflected from the periphery of the perforated mirror 8, passes through the objective lens 2 and the pupil Ep of the eye E to be examined, and illuminates the fundus Er.

Then, infrared light reflected from the fundus Er passes through the pupil Ep, the objective lens 2, and the perforated mirror 8, transmits through the focus lens 9, the imaging lens 10, and the quick return mirror 11 that transmits infrared light, and forms an image on the image sensor 23 of the imaging camera C.

Thus, infrared light emitted from the observation light source 1 is reflected from the fundus Er, forms an image on the image sensor 23 as a fundus image, and can be observed on the moving image observation monitor 25 as a moving image. The state of observation in the imaging camera C is a state of live view itself.

Figure 2:
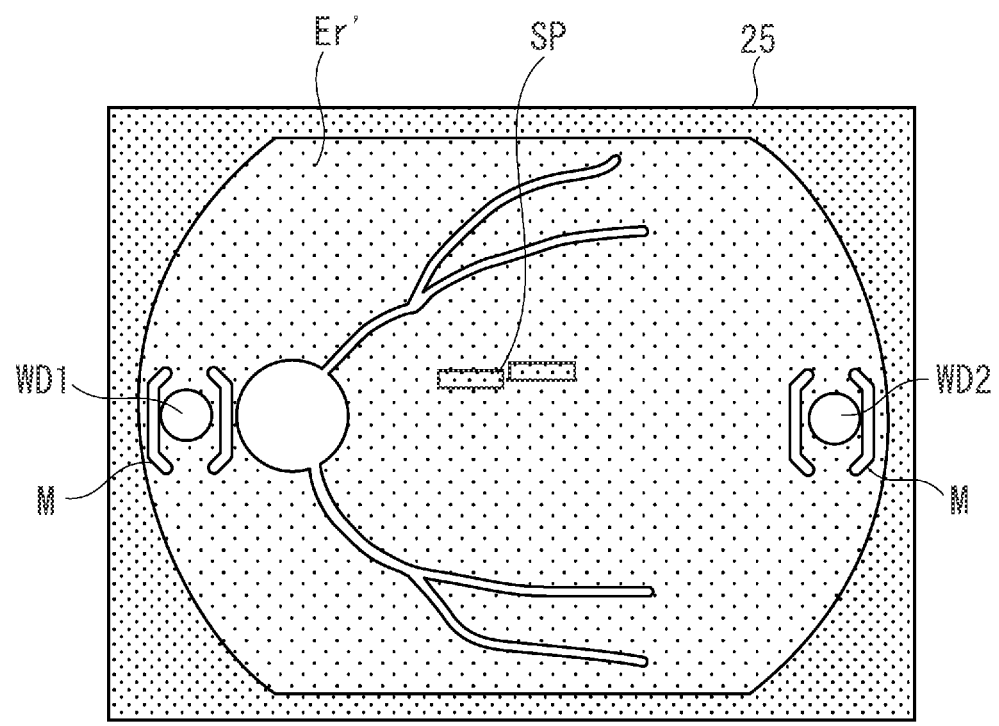
FIG. 2 illustrates a state of observation according to the first exemplary embodiment of the present invention.

On the other hand, each of luminous fluxes emitted from the alignment index projection system and the focus index projection system (not illustrated) is reflected from the fundus Er and the cornea of the eye E to be examined, and forms an image on the image sensor 23. On the moving image observation monitor 25 illustrated in FIG. 2, with an observation image Er' of the fundus Er, alignment indexes WD1 and WD2, and focus index SP are displayed. Thus, these are observable.

An examiner performs not only the alignment of the eye E to be examined with the fundus camera, but also focus adjustment to the fundus Er in such a manner that the alignment indexes WD1 and WD2 enter a respective alignment range M, and two focus indexes SP become horizontally straight.

At this time, in order to guide the reflected image from the fundus Er, the alignment indexes WD1 and WD2, and the focus indexes SP onto the image sensor 23, the quick return mirror 21 of the imaging camera C is retracted from the optical path on the fundus imaging optical system O2.

Further, a mechanical shutter control unit of the first curtain 22a and the second curtain 22b is in an open state. By this control, alignment of the eye E to be examined can be performed using the moving image observation monitor 25 of the imaging camera C. Furthermore, with this control by the imaging camera C, a live view function is achieved.

In a state in which the live view function on the imaging camera C is not used, the quick return mirror 21 is inserted in the optical path of the fundus imaging optical system O2. Further, the first curtain 22a is in the state of light shielding. Thus, the reflected image from the fundus Er, the alignment indexes WD1 and WD2, and the focus indexes SP cannot be guided onto the image sensor 23.

FIG. 3A is a flowchart illustrating an operation in imaging a still image. An examiner presses an imaging start switch on the input unit 33 after alignment of the eye E to be examined ends. The system control unit 31 executes processing in step S1 in response to the start signal to start imaging control.

In step S2, in order to guide visible light from the imaging light source 4 to the image sensor 23, the system control unit 31 retracts the quick return mirror 11 from the fundus imaging optical system O2. Further, in order not to capture unnecessary light in imaging a still image, the observation light source 1, the internal fixation lamp 12, the alignment indexes WD1 and WD2, and the focus indexes SP are turned off.

Figure 3B:
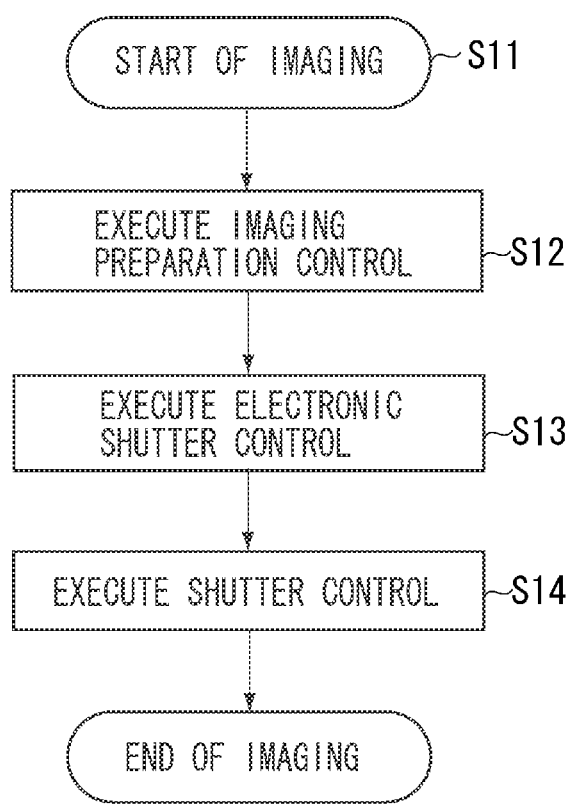

When the imaging preparation control in step S2 ends, in step S3, the system control unit 31 executes imaging start control of the imaging camera C. In the imaging camera C, in response to operation in step S3, imaging start processing in step S11 of the imaging camera C in FIG. 3B is executed. The control of the imaging camera C will be described below.

The system control unit 31 also executes processing in step S4 on the fundus camera to be executed after the processing in step S3 ends. This processing is repeated until the end time of the electronic shutter control elapses. In other words, this processing is wait processing until electronic shutter control to be executed inside the imaging camera C ends. Next, when wait processing ends (YES in step S4), the processing proceeds to step S5. In step S5, the system control unit 31 outputs a radiation command to the imaging light source control unit 32 to activate the imaging light source 4.

Visible light thus emitted from the imaging light source 4 passes through the fundus illumination optical system O1, and then, reflected from the fundus Er of the eye E to be examined. A fundus-reflected image passes through the fundus imaging optical system O2 to be formed on the image sensor 23. Finally, in step S6, the system control unit 31 executes imaging end processing, which is a step opposite the imaging preparation control executed in step S2.

In a flowchart illustrated in FIG. 3B, imaging start processing in step S11 is executed by a change from the processing in step S3 on the fundus camera to the imaging camera control unit 26. Subsequent to the processing in step S11, in step S12, setting change processing or the like for imaging is executed by the imaging camera control unit 26.

After processing in step S12, which is imaging preparation processing, ends, then in step S13, the imaging camera control unit 26 causes the electronic shutter control unit 27 to execute electronic shutter control. Thereafter, in step S14, the imaging camera control unit 26 executes shutter control processing. Then, imaging control ends.

Thus, in each imaging control of the fundus camera and the imaging camera C, emitting control of the imaging light source 4 to be executed in step S5 is executed between the electronic shutter control in step S13 and the shutter control in step S14.

FIGS. 4A, 4B are timing charts illustrating the state of imaging control in the imaging camera C. In FIG. 4, "open" represents a state where an optical path is not intercepted, and "closed" represents a state where an optical path is intercepted. Further, operations of the quick return mirror 21, the first curtain 22a, and the second curtain 22b are illustrated therein. Respective steps indicate the steps in which the processing described in the flowcharts illustrated in FIGS. 3A and 3B is executed.

Electronic shutter control indicated by a vertical dotted line is executed at the timing of step S13 after the imaging start in step S1. The shutter control is executed at the timing in step S14. Emitting control in step S5 is executed between steps S13 and S14.

Thus, light received by the image sensor 23, until immediately before the electronic shutter control, is refreshed by the electronic shutter control in step S13, and recorded as a still image after shutter control in step S14 ends. In other words, only the reflected image of the fundus Er irradiated by the imaging light source 4 in step S5 is stored on the image sensor 23 to be recordable as a still image.

As illustrated in FIG. 4A, until processing in steps S1 to S14 are executed, all of the quick return mirror 21, the first curtain 22a, and the second curtain 22b are in an open state. In other words, irradiation control will be executed in step S5 while the distinctive live view function described in the first moving image observation unit is used. It is obvious that this control is distinctive control in the present exemplary embodiment when compared with the following FIG. 4B.

FIG. 4B is a timing chart illustrating an imaging control when the live view function is not used. A difference from FIG. 4A is that each of the quick return mirror 21 and the first curtain 22a is changed from a closed state to an open state until steps S1 to S14 are executed.

Normally, an X contact signal, which is an open signal of the shutter screen 22 of the imaging camera C, is output when the first curtain 22a is changed from a closed state to an open state. In synchronization with this X contact signal, in step S5, irradiation control is executed.

Thus, in FIG. 4A, electronic shutter control in step S13 substitute the control in which the first curtain 22a is changed from a closed state to an open state executed in FIG. 4B. In other words, a movement in which the first curtain 22a is changed from a closed state to an open state will be achieved by the electronic shutter control in step S13.

Accordingly, light, which is received by the image sensor 23 until directly before electronic shutter control, is refreshed after execution of step S13. Only the reflected light from the fundus Er irradiated by the imaging light source 4 in step S5 is stored in the image sensor 23 and recorded as a still image.

Further, processing H illustrated in FIG. 4A is processing to be added when imaging control using the first curtain 22a illustrated in FIG. 4B is executed from a state in which a live view function described in the first moving image observation unit has been used. However, this processing H is unnecessary processing as obvious referring to FIG. 4A. Furthermore, owing to the processing H of this first curtain 22a, time from step S1 to step S5 may also be required. Owing to this time, the fixation position of the eye E to be examined may also move and the blink may also occur.

As described above, the processing H is not executed. Thus, time period from when the imaging start operation is executed until the imaging is actually executed can be minimized. A movement of the fixation position of the eye E to be examined and an occurrence of the blinks at the moment of imaging can be prevented. Accordingly, failure of imaging is prevented.

The fundus camera according to the first exemplary embodiment is a non-mydriatic fundus camera and observes by the moving image observation monitor 25 of the imaging camera C using near infrared light by which the eye E to be examined does not feel glare.

Accordingly, not only an image sufficient for observation can be obtained but also a load to be imposed on the eye E to be examined can be reduced. Thus, not only characteristics of the non-mydriatic fundus camera are retained but also a digital camera such as the imaging camera C, which is generally used, can be used.

Further, since the live view function is used for observation, the observation optical system is not needed to be configured by a dedicated sensor such as a CCD for executing observation. Thus, an apparatus can be simplified.

Figure 5:
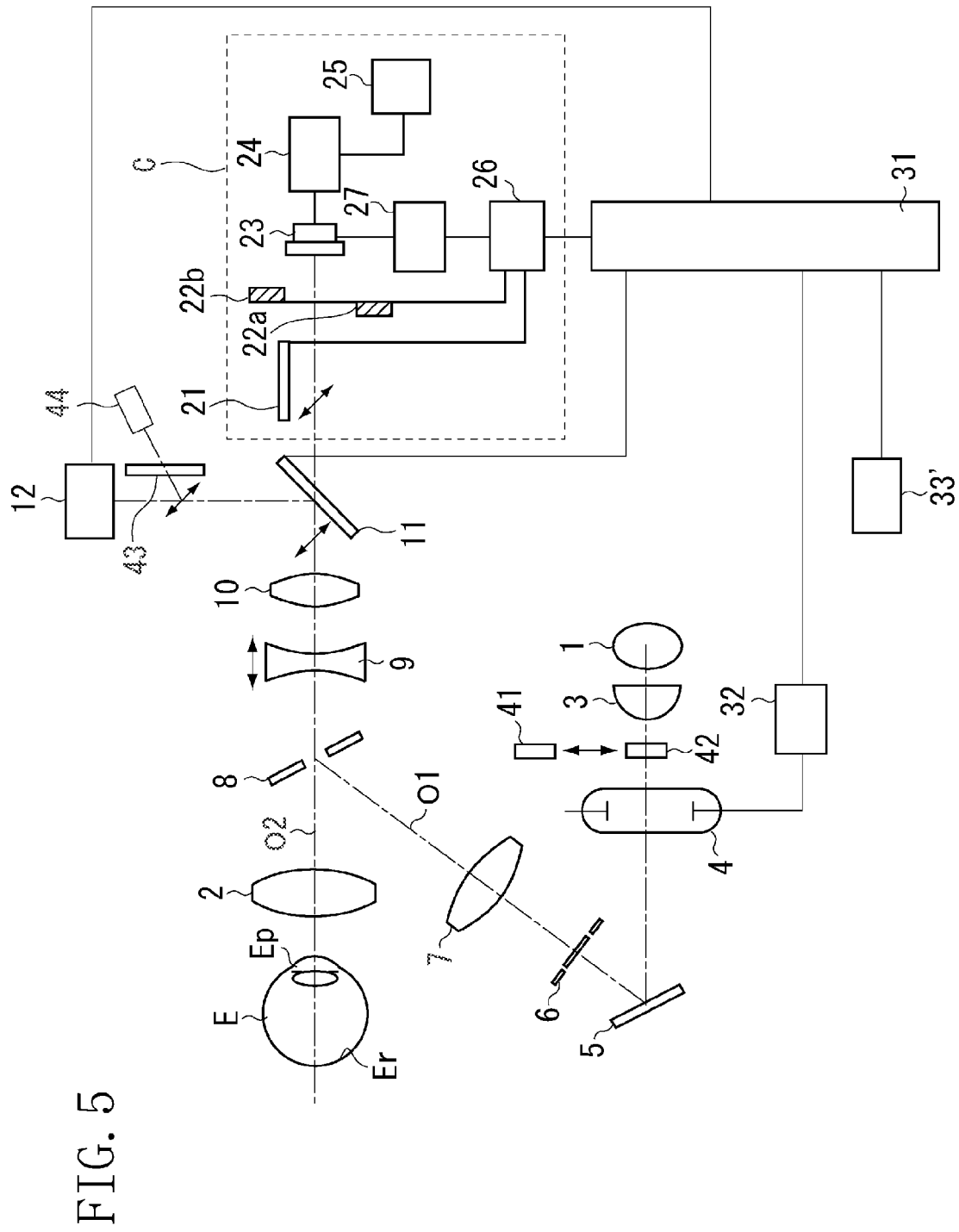
FIG. 5 is a configuration diagram illustrating a non-mydriatic mode according to a second exemplary embodiment of the present invention.

FIG. 5 is a configuration diagram illustrating a mydriatic/non-mydriatic-integrated type fundas camera integrated with a mydriatic and non-mydriatic fundas camera according to a second exemplary embodiment. Components having the same reference numerals as those in the first exemplary embodiment are designated by the same reference numerals.

Compared with FIG. 1 according to the first exemplary embodiment, an infrared light cut filter 41 and a visible light cut filter 42 are added between the condenser lens 3 and the imaging light source 4 in the fundus illumination optical system O1, and an attachable/detachable reflection mirror 43 and a direct viewing finder 44 are provided in the optical path of the internal fixation lamp 12.

Either of the infrared light cut filter 41 and the visible light cut filter 42 can be attached and detached in the optical path. Further, the reflection mirror 43 is provided between the quick return mirror 11 and the internal fixation lamp 12 to allow light to be guided to the direct viewing finder 44 that enables an examiner to perform finder observation of the eye E to be examined by visible light.

An input unit 33' is functionally different from that in the first exemplary embodiment. In addition to the imaging start switch, a mydriatic/non-mydriatic selection switch for changing the state of observation between a mydriatic mode and a non-mydriatic mode is provided. Further, in the first exemplary embodiment, the observation light source 1 is an LED that emits infrared light. However, in the second exemplary embodiment, the observation light source 1 is a halogen lamp that emits visible light.

In the second exemplary embodiment, first, the mydriatic/non-mydriatic selection switch provided on the input unit 33' is operated to select a change between the mydriatic mode and the non-mydriatic mode. The attachable/detachable reflection mirror 43 is detached from the optical path in a direction of reflection from the quick return mirror 11. The visible light cut filter 42 is inserted into the fundus illumination optical system O1.

Visible light emitted from the observation light source 1 passes through the condenser lens 3 and only infrared light transmits through the visible light cut filter 42. The infrared light transmitting through the visible light cut filter 42 passes through the imaging light source 4 and reflected from the mirror 5. The processing until an image is formed on the image sensor 23 is similar to that in the first exemplary embodiment.

Accordingly, the visible light emitted from the observation light source 1 includes only infrared light, and the infrared light reflected from the fundus Er, and then forms an image on the image sensor 23. The image can be observed on the moving image observation monitor 25 as a fundus image Er' with a moving image, and alignment can be performed similarly to the first exemplary embodiment. The attachable/detachable reflection mirror 43 is detached from the optical path in a direction of reflection from the quick return mirror 11 to allow observation by the direct viewing finder 44 while guiding light from the internal fixation lamp 12 to the eye E to be examined.

Further, the imaging control is similar to that in the first exemplary embodiment. The effect thereof is also similar thereto. More specifically, in the non-mydriatic mode, on the moving image observation monitor 25, observation is executed through the first moving image observation unit, and in imaging a still image, electronic shutter processing is executed by the electronic shutter control unit 27.

Figure 6:
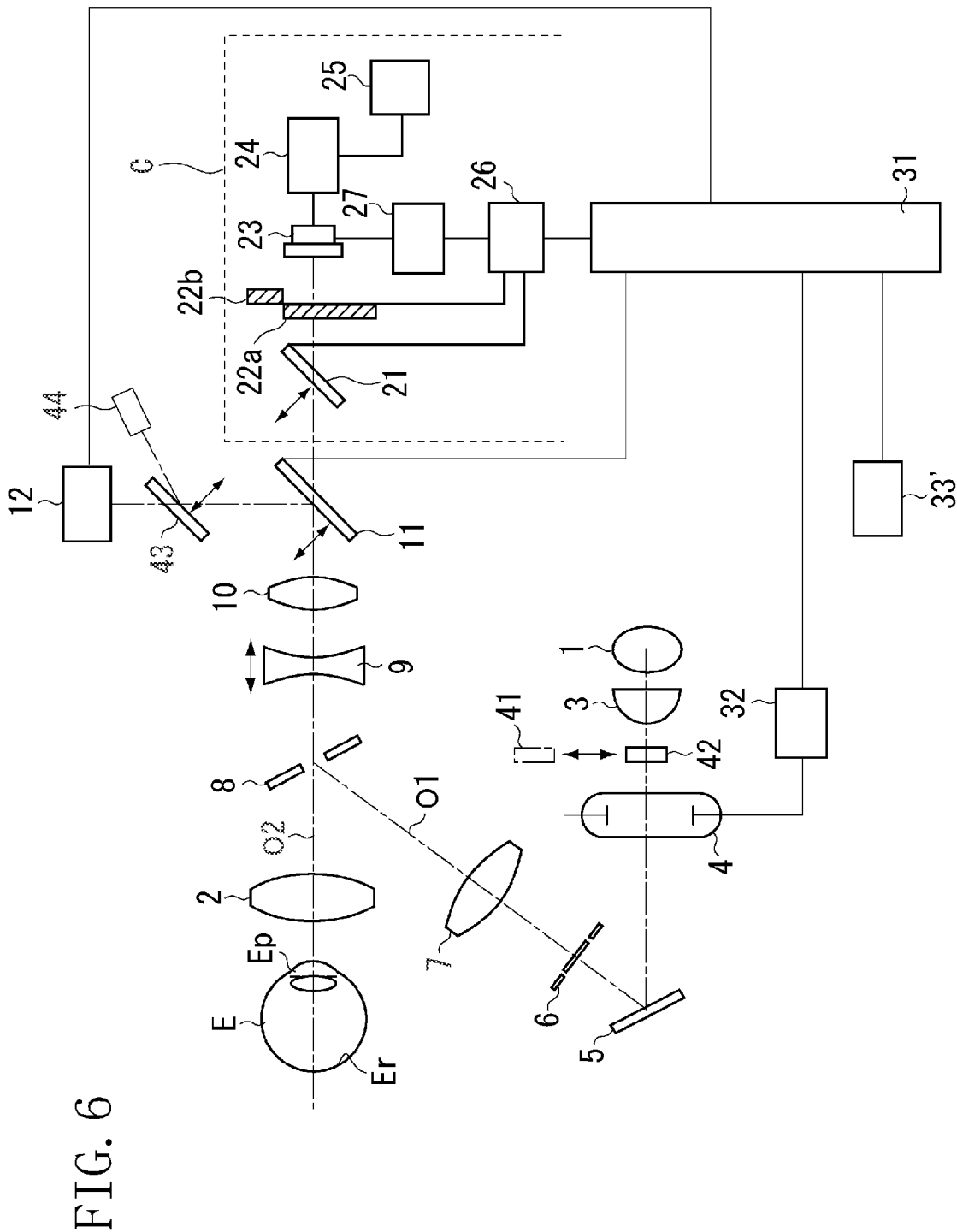
FIG. 6 is a configuration diagram illustrating a mydriatic mode according to a second exemplary embodiment.

When the mydriatic mode is selected, as illustrated in FIG. 6, the attachable/detachable reflection mirror 43 is inserted into the optical path in a direction of reflection from the quick return mirror 11 and the infrared light cut filter 41 is inserted into the fundus illumination optical system O1. The visible light emitted from the observation light source 1 passes through the condenser lens 3, an infrared light component is cut by the infrared light cut filter 41, and then is transmitted.

The fundus image of the fundus Er passes through the objective lens 2, the focus lens 9, and the imaging lens 10, and returns to the quick return mirror 11. However, since the quick return mirror 11 reflects visible light, the visible light is reflected thereby in a direction of the fundus image reflection mirror 43 and can be observed by the second moving image observation unit by the direct viewing finder 44. Thus, differently from the first exemplary embodiment, direct view observation using visible light is performed by an examiner. Thus, alignment of the eye E to be examined can be executed.

Further, the imaging control is similar to the control described referring to FIG. 4B in the first exemplary embodiment. The imaging control in this case is a general imaging method using the imaging camera C. More specifically, in the mydriatic mode, observation is executed by the direct viewing finder 44. During imaging, imaging control using the first curtain 22a is executed.

Thus, the control according to the second exemplary embodiment, according to the selection between the mydriatic mode and the non-mydriatic mode, in the non-mydriatic mode, observation is executed using the moving image observation monitor 25 and imaging control using electronic shutter processing is executed. In the mydriatic mode, observation is executed using the direct viewing finder 44 and imaging control using the first curtain 22a is executed.

In the fundus camera according to the second exemplary embodiment, control similar to that of the non-mydriatic fundus camera described in the first exemplary embodiment is executed in the non-mydriatic mode. Thus, similar to the first exemplary embodiment, a dedicated sensor such as a CCD for executing observation and an observation optical system are not required. Accordingly, an apparatus can be simplified.

Particularly, as the second exemplary embodiment, an apparatus having both functions of a mydriatic mode and a non-mydriatic mode generally tends to be complicated. Thus, the effect is significant. Further, similar to the first exemplary embodiment, time period from when an imaging start operation is executed until imaging is actually executed can be minimized. Accordingly, a movement of a fixation position of a subject's eye and an occurrence of the blinks at the moment of imaging can be prevented. Thus, failure of imaging can be prevented.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-196997 filed Aug. 27, 2009, which is hereby incorporated by reference herein in its entirety.

What is claimed is:

1. An ophthalmologic imaging apparatus comprising:
    a first light source configured to generate infrared light for illuminating a subject's eye via an illumination optical system;
    a second light source configured to generate visible light for illuminating the subject's eye via the illumination optical system;
    an imaging unit including a receiving surface configured to receive light returned from the subject's eye illuminated with the infrared light via an imaging optical system, the imaging unit being used both as an imaging device configured to capture a moving image of the subject's eye illuminated with the infrared light and as an imaging device configured to capture a still image of the subject's eye illuminated with the visible light;
    an electronic shutter control unit configured to refresh, by electronic shutter processing, charge caused by light received by the imaging unit after turning off the first light source;
    an irradiation control unit configured to control the second light source to generate the visible light after the charge is refreshed; and
    an obtaining unit configured to obtain a still image of the subject's eye based on charge caused by light returned from the subject's eye illuminated with the visible light and received by the receiving surface via the imaging optical system.

2. The ophthalmologic imaging apparatus according to claim 1, further comprising:
    a first curtain and a second curtain provided on the front of the imaging unit; and
    a mechanical shutter control unit configured to close the second curtain after the second light source generates the visible light,
        wherein the obtaining unit obtains, in a state of opening the first curtain, a moving image of the subject's eye based on charge caused by light received by the imaging unit before turning off the first light source, and
        wherein the electronic shutter control unit refreshes, by the electronic shutter processing in the state of opening the first curtain, charge caused by light received by the imaging unit after the turning off the first light source.

3. The ophthalmologic imaging apparatus according to claim 1, wherein the electronic shutter control unit refreshes, after the first light source is turned off in response to a start signal for starting to acquire a still image of the subject's eye using the visible light, charge caused by light received by the imaging unit in response to the start signal.

4. The ophthalmologic imaging apparatus according to claim 3, further comprising an index projection unit configured to project an index onto the subject's eye,
    wherein the electronic shutter control unit refreshes, after the first light source and the index projection unit are turned off, charge caused by light received by the imaging unit in response to the start signal.

5. The ophthalmologic imaging apparatus according to claim 3, further comprising an imaging start switching unit configured to generate the start signal,
    wherein the electronic shutter control unit receives the start signal.

6. The ophthalmologic imaging apparatus according to claim 1, wherein the electronic shutter processing achieves an advantage of a movement in which a first curtain is changed from a closed state to an open state.

7. A camera detachable from an ophthalmologic imaging apparatus containing an illumination optical system configured to illuminate a subject's eye, and an imaging optical system configured to the subject's eye illuminated with one of infrared light and visible light by the illumination optical system, the camera comprising:
    an imaging unit including a receiving surface configured to receive light returned from the subject's eye illuminated with the infrared light via the imaging optical system;
    an electronic shutter control unit configured to refresh, by electronic shutter processing, charge caused by light received by the imaging unit after turning off a first light source configured to generate the infrared light for illuminating the subject's eye via the illumination optical system; and
    an obtaining unit configured to obtain a still image of the subject's eye based on charge caused by light returned from the subject's eye illuminated with a visible light and received by the receiving surface via the imaging optical system, wherein the visible light is generated by a second light source configured to generate the visible light for illuminating the subject's eye via the illumination optical system.

8. The camera according to claim 7, further comprising:
    a first curtain and a second curtain provided on the front of the imaging unit;

a mechanical shutter control unit configured to close the second curtain after the second light source generates the visible light, wherein the obtaining unit obtains, in a state of opening the first curtain, a moving image of the subject's eye based on charge caused by light received by the imaging unit before the turning off the first light source, and wherein the electronic shutter control unit refreshes, by the electronic shutter processing in the state of opening the first curtain, charge caused by light received by the imaging unit after the turning off the first light source.

9. The camera according to claim 7, wherein the electronic shutter control unit refreshes, after the first light source is turned off in response to a start signal for starting to acquire a still image of the subject's eye using the visible light, charge caused by light received by the imaging unit in response to the start signal.

10. The camera according to claim 9, wherein the electronic shutter control unit refreshes, after the first light source and an index projection unit configured to project an index onto the subject's eye are turned off in response to the start signal, charge caused by light received by the imaging unit in response to the start signal.

11. The camera according to claim 9, wherein the electronic shutter control unit receives the start signal from an imaging start switching unit configured to generate the stat signal.

12. The camera according to claim 7, wherein the electronic shutter processing achieves an advantage of a movement in which a first curtain is changed from a closed state to an open state.

13. The camera according to claim 7, wherein the imaging unit is used both as an imaging device configured to capture a moving image of the subject's eye illuminated with the infrared light and as an imaging device configured to capture a still image of the subject's eye illuminated with the visible light.

14. An ophthalmologic imaging method comprising:
refreshing, by electronic shutter processing, charge caused by light received by an imaging unit after turning off a first light source configured to generate infrared light for illuminating a subject's eye via an illumination optical system, wherein the imaging unit includes a receiving surface configured to receive light returned from the subject's eye illuminated with the infrared light via an imaging optical system;
controlling a second light source to generate visible light after the charge is refreshed, wherein the second light source generates the visible light for illuminating the subject's eye via the illumination optical system; and
obtaining a still image of the subject's eye based on charge caused by light returned from the subject's eye illuminated with the visible light and received by the receiving surface via the imaging optical system.

15. The ophthalmologic imaging method according to claim 14, further comprising:
obtaining, in a state of opening a first curtain provided on the front of the imaging unit, a moving image of the subject's eye based on charge caused by light received by the imaging unit before the turning off the first light source, and
closing a second curtain provided on the front of the imaging unit after the second light source generates the visible light,
wherein in the refreshing step, refreshes, by the electronic shutter processing in the state of opening the first curtain, charge caused by light received by the imaging unit after the turning off the first light source.

16. The ophthalmologic imaging method according to claim 14, wherein in refreshing step, refreshing, after the first light source is turned off in response to a start signal for starting to acquire a still image of the subject's eye using the visible light, charge caused by light received by the imaging unit in response to the start signal.

17. The ophthalmologic imaging method according to claim 16, wherein in refreshing step, refreshing, after the first light source and an index projection unit configured to project an index onto the subject's eye are turned off in response to the start signal, charge caused by light received by the imaging unit in response to the start signal.

18. The ophthalmologic imaging method according to claim 16, further comprising:
receiving the start signal from an imaging start switching unit configured to generate the stat signal.

19. A non-transitory computer-readable recording medium storing a program that causes a computer to execute the ophthalmologic imaging method according to claim 14.

20. The ophthalmologic imaging method according to claim 14, wherein the electronic shutter processing achieves an advantage of a movement in which a first curtain is changed from a closed state to an open state.

21. The ophthalmologic imaging method according to claim 14, wherein the imaging unit is used both as an imaging device configured to capture a moving image of the subject's eye illuminated with the infrared light and as an imaging device configured to capture a still image of the subject's eye illuminated with the visible light.

22. An ophthalmologic imaging apparatus comprising:
a first light source configured to generate infrared light for illuminating a subject's eye via an illumination optical system;
a second light source configured to generate visible light for illuminating the subject's eye via the illumination optical system;
an imaging unit including a receiving surface configured to receive light returned from the subject's eye illuminated with the infrared light via an imaging optical system;
a first curtain and a second curtain provided on the front of the imaging unit;
an obtaining unit configured to obtain, in a state that the first curtain is opened, a moving image of the subject's eye based on charge caused by light received by the imaging unit when the first light source is turned on;
a control unit configured to refresh, in the state that the first curtain is opened, charge caused by light received by the imaging unit after turning off the first light source; and
an irradiation control unit configured to control the second light source to generate the visible light after the charge is refreshed;
wherein the obtaining unit obtains a still image of the subject's eye based on charge caused by light returned from the subject's eye illuminated with the visible light and received by the receiving surface via the imaging optical system.

23. The ophthalmologic imaging apparatus according to claim 22, further comprising: a mechanical shutter control unit configured to close the second curtain after the second light source generates the visible light.

24. The ophthalmologic imaging apparatus according to claim 22, wherein the imaging unit is used both as an imaging device configured to capture a moving image of the subject's eye illuminated with the infrared light and as an imaging device configured to capture a still image of the subject's eye illuminated with the visible light.

25. An ophthalmologic imaging apparatus comprising:
a first light source configured to generate infrared light for illuminating a subject's eye via an illumination optical system;
a second light source configured to generate visible light for illuminating the subject's eye via the illumination optical system;
an imaging unit including a receiving surface configured to receive light returned from the subject's eye illuminated with the infrared light via an imaging optical system;
a control unit configured to refresh, after turning off the first light source in response to a start signal for starting to acquire a still image of the subject's eye using the visible light, charge caused by light received by the imaging unit in response to the start signal;
an irradiation control unit configured to control the second light source to generate the visible light after the charge is refreshed; and
an obtaining unit configured to obtain a still image of the subject's eye based on charge caused by light returned from the subject's eye illuminated with the visible light and received by the receiving surface via the imaging optical system.

26. The ophthalmologic imaging apparatus according to claim 25, further comprising an index projection unit configured to project an index onto the subject's eye,
wherein the control unit refreshes, after the first light source and the index projection unit are turned off, charge caused by light received by the imaging unit in response to the start signal.

27. The ophthalmologic imaging apparatus according to claim 25, further comprising an imaging start switching unit configured to generate the start signal,
wherein the control unit receives the start signal when the imaging start switching unit generates the start signal.

28. The ophthalmologic imaging apparatus according to claim 25, wherein the imaging unit is used both as an imaging device configured to capture a moving image of the subject's eye illuminated with the infrared light and as an imaging device configured to capture a still image of the subject's eye illuminated with the visible light.

29. A control method for an ophthalmologic imaging apparatus comprising:
generating, by a first light source, infrared light for illuminating a subject's eye via an illumination optical system;
generating, by a second light source, visible light for illuminating the subject's eye via the illumination optical system;
receiving, via a receiving surface of an imaging unit, light returned from the subject's eye illuminated with the infrared light via an imaging optical system;
obtaining, in a state that a first curtain on the front of the imaging unit is opened, a moving image of the subject's eye based on charge caused by light received by the imaging unit when the first light source is turned on;
refreshing, in the state that the first curtain is opened, charge caused by light received by the imaging unit after turning off the first light source;
controlling the second light source to generate the visible light after the charge is refreshed; and
obtaining a still image of the subject's eye based on charge caused by light returned from the subject's eye illuminated with the visible light and received by the receiving surface via the imaging optical system,
wherein both the first curtain and a second curtain are provided on the front of the imaging unit.

30. The control method according to claim 29, further comprising: closing, via a mechanical shutter control unit, the second curtain after the second light source generates the visible light.

31. A non-transitory computer-readable recording medium storing a program that causes a computer to execute the control method according to claim 29.

32. The control method for an ophthalmologic imaging apparatus according to claim 29, wherein the imaging unit is used both as an imaging device configured to capture a moving image of the subject's eye illuminated with the infrared light and as an imaging device configured to capture a still image of the subject's eye illuminated with the visible light.

33. A control method for an ophthalmologic imaging apparatus comprising:
generating, by a first light source, infrared light for illuminating a subject's eye via an illumination optical system;
generating, by a second light source, visible light for illuminating the subject's eye via the illumination optical system;
receiving, via a receiving surface of an imaging unit, light returned from the subject's eye illuminated with the infrared light via an imaging optical system;
refreshing, after turning off the first light source in response to a start signal for starting to acquire a still image of the subject's eye using the visible light, charge caused by light received by the imaging unit in response to the start signal;
controlling the second light source to generate the visible light after the charge is refreshed; and
obtaining a still image of the subject's eye based on charge caused by light returned from the subject's eye illuminated with the visible light and received by the receiving surface via the imaging optical system.

34. The control method according to claim 33, further comprising:
projecting an index onto the subject's eye via a projection unit; and
refreshing, after the first light source and the index projection unit are turned off, charge caused by light received by the imaging unit in response to the start signal.

35. The control method according to claim 33, further comprising:
generating a start signal via an imaging start switching unit; and
receiving the start signal when the imaging start switching unit generates the start signal.

* * * * *